(12) United States Patent
Li et al.

(10) Patent No.: US 9,861,131 B2
(45) Date of Patent: Jan. 9, 2018

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Hongyong Luo, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 542 days.

(21) Appl. No.: 14/550,998

(22) Filed: Nov. 22, 2014

(65) Prior Publication Data

US 2015/0144147 A1    May 28, 2015

(30) Foreign Application Priority Data

Nov. 25, 2013 (CN) .................... 2013 2 0749450 U

(51) Int. Cl.
*A24F 47/00* (2006.01)
*F22B 1/28* (2006.01)

(52) U.S. Cl.
CPC ............ *A24F 47/008* (2013.01); *F22B 1/284* (2013.01)

(58) Field of Classification Search
CPC ..... A24F 47/008; A24F 47/004; A24F 47/002
See application file for complete search history.

(56) References Cited

U.S. PATENT DOCUMENTS

| | | | |
|---|---|---|---|
| 2013/0152922 A1* | 6/2013 | Benassayag | A61M 15/06 128/202.21 |
| 2013/0192623 A1* | 8/2013 | Tucker | H01C 17/00 131/329 |
| 2014/0360514 A1* | 12/2014 | Zhu | A24F 47/008 131/329 |
| 2015/0013700 A1* | 1/2015 | Liu | A24F 47/008 131/329 |

* cited by examiner

*Primary Examiner* — Anthony Calandra
(74) *Attorney, Agent, or Firm* — Cheng-Ju Chiang

(57) ABSTRACT

An exemplary atomizer for an electronic cigarette includes an atomizing tube, an atomizing assembly, a first fixing sleeve arranged at a first end of the atomizing tube, and a fixing tube received in the first end of the atomizing tube adjacent to the first fixing sleeve. The fixing tube receives the atomizing assembly and is connected to the first fixing sleeve. The atomizing tube defines a liquid reservoir. The fixing tube defines a liquid guiding chamber.

13 Claims, 3 Drawing Sheets

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

An electronic cigarette includes an atomizer and a battery assembly. The atomizer includes a liquid reservoir for storing tobacco liquid and an atomizing assembly for atomizing the tobacco liquid. The battery assembly is configured for powering the atomizer.

In a typical atomizer, the atomizing assembly is in direct contact with the tobacco liquid in the liquid reservoir. However, after long time contact with the tobacco liquid, the chemicals in the atomizing assembly may pollute the tobacco liquid. The polluted tobacco liquid may be harmful for users of the electronic cigarette.

What is needed, therefore, is an atomizer and an electronic cigarette using same, which can overcome the above shortcomings.

SUMMARY

An exemplary atomizer for an electronic cigarette includes an atomizing tube, an atomizing assembly, a first fixing sleeve arranged at a first end of the atomizing tube; and a fixing tube received in the first end of the atomizing tube adjacent to the first fixing sleeve. The fixing tube receives the atomizing assembly and is connected to the first fixing sleeve. The atomizing tube defines a liquid reservoir. The fixing tube defines a liquid guiding chamber.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Embodiments of the present disclosure will now be described in detail below and with references to the drawings.

Figure 1:
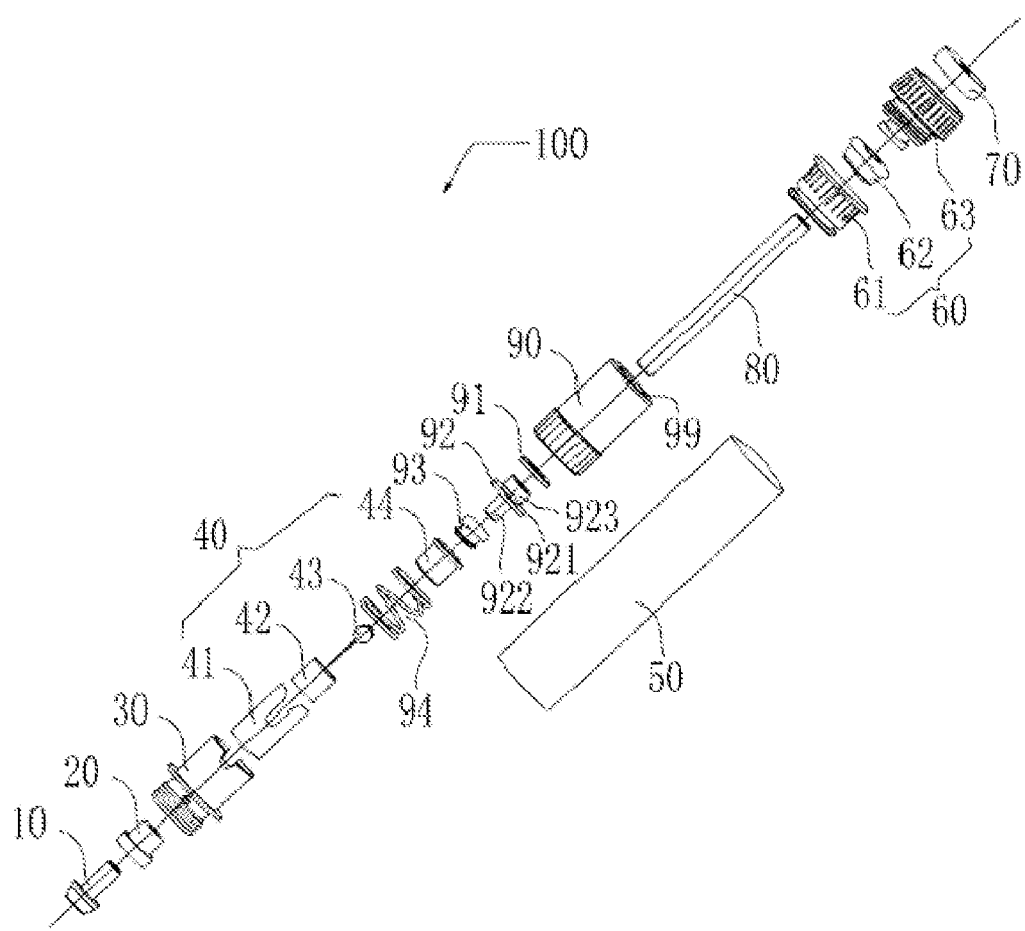
FIG. 1 is an exploded perspective view of an atomizer according to a first embodiment.

Referring to FIG. 1, an atomizer 100 for an electronic cigarette includes a tubular electrode 10, an insulated ring 20, a first fixing sleeve 30, an atomizing assembly 40, an atomizing tube 50, a second fixing sleeve 60, a mouthpiece cover 70, an air pipe 80, a fixing tube 90, a seal ring 91, a pushing element 92, a silicone ring 93, and a spring 94. The atomizing assembly 40 includes a tube 41, a fixing sleeve 42 for fixing a heating wire, a heating wire component 43, and a cover 44. The second fixing sleeve 60 includes an internal screw sleeve 61, a seal sleeve 62, and an external screw sleeve 63.

Figure 2:
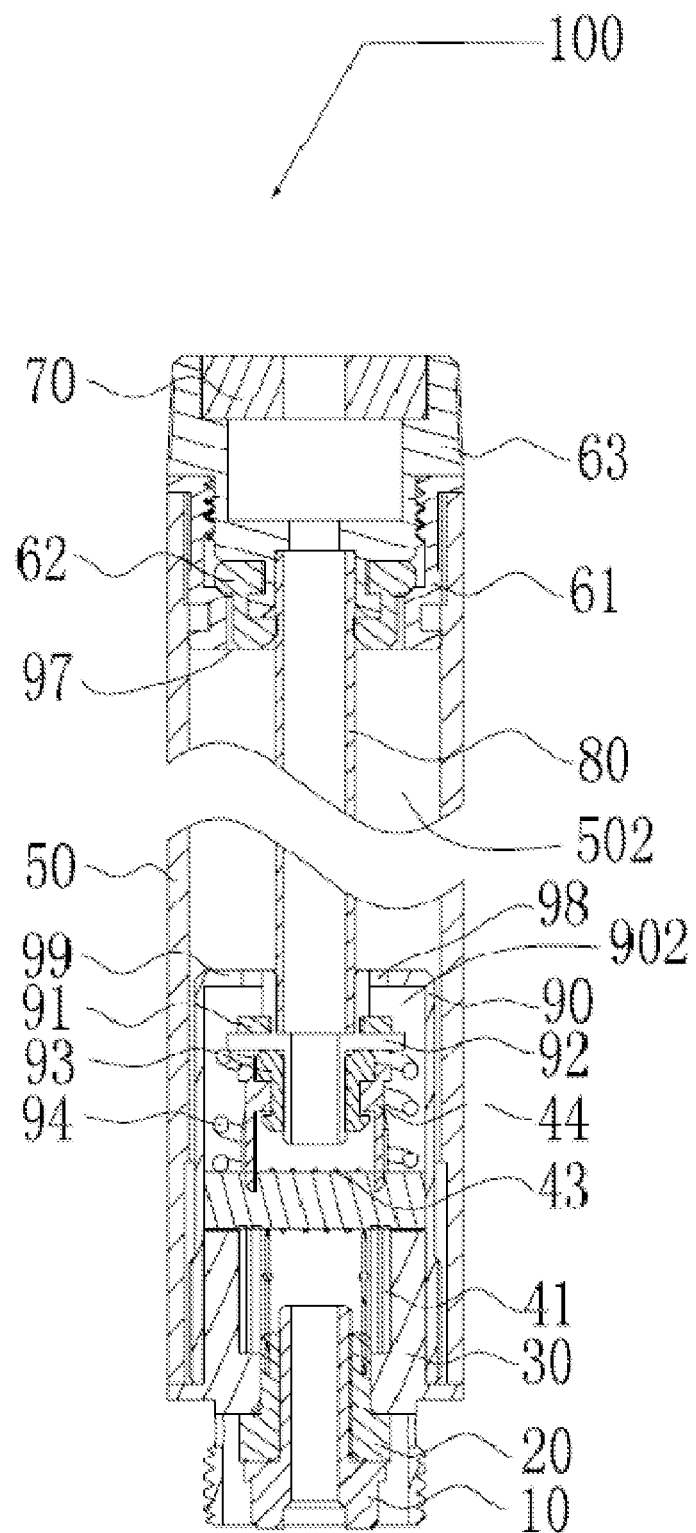
FIG. 2 is a cross-sectional view of the atomizer of FIG. 1.

Referring to FIG. 2, the tubular electrode 10 is fixed in the first fixing sleeve 30 via the insulated ring 20. The tube 41 is fixedly connected with the first fixing sleeve 30. The fixing sleeve 42 is engaged in the tube 41. The heating wire component 43 is fixed in the fixing sleeve 42. The cover 44 covers the heating wire component 43 and the fixing sleeve 42, and fixes the heating wire component 43 and the fixing sleeve 42 in the tube 41. In other embodiments, the tube 41 and the first fixing sleeve 30 may be integrally formed.

The fixing tube 90 is arranged at one end of the atomizing tube 50 adjacent to the first fixing sleeve 30. The fixing tube 90 receives the atomizing assembly 40, and is connected to the first fixing tube 30. The spring 94 and the pushing element 92 are arranged in the fixing tube 90. The pushing element 92 sequentially includes a first tube body 922, a flange 921, and a second tube body 923. The cover 44 defines a through hole, and the first tube body 922 is hermetically coupled to the through hole via the silicone ring 93. One end of the spring 94 abuts against the first fixing sleeve 30, and the other end of the spring 94 abuts against the flange 921. The fixing tube 90 includes a top wall 99 defining an opening. A first end of the air pipe 80 passes through the opening, and is fixedly connected with the second tube body 923, while a second end of the air pipe 80 is held against the second fixing sleeve 60. An outer wall of the air pipe 80 and an inner wall of the opening cooperatively define a liquid guiding hole 98. The seal ring 91 is wrapped around the second tube body 923, and is configured (i.e., structured and arranged) for sealing the liquid guiding hole 98.

Two ends of the atomizing tube 50 are fixedly connected to the first fixing sleeve 30 and the second fixing sleeve 60. The internal screw sleeve 61 is fixedly connected with the atomizing tube 50. The internal screw sleeve 61 and the air pipe 80 cooperatively define a liquid injection hole 97. The seal sleeve 62 is adapted for sealing the liquid injection hole 97. When the external screw sleeve 63 is screwed off and the seal sleeve 62 is pulled out, tobacco liquid is filled into a liquid reservoir 502 defined by the atomizing tube 50 via the liquid injection hole 97. The mouthpiece cover 70 is engaged with the external screw sleeve 63. It is to be understood that in other embodiments, the mouthpiece cover 70 and the external screw sleeve 63 may be integrally formed.

In the present embodiment, the atomizer 100 includes the liquid reservoir 502 and a liquid guiding chamber 902 defined by the fixing tube 90. The atomization process occurs in the fixing tube 90. Accordingly, the tobacco liquid in the liquid reservoir 502 is prevented from polluted.

The atomizer 100 can prevent leakage of the tobacco liquid. When the external screw sleeve 63 is screwed off a certain degree, the pushing element 92 is moved upwards upon the elastic force of the spring 94, the liquid guiding hole 98 is sealed by the seal ring 91, and the liquid guiding chamber 902 is sealed. In this position, since a stroke of the pushing element 92 is less than that of the external screw sleeve 63, the external screw sleeve 63 and the internal screw sleeve 61 are still hermetically coupled. Then the external screw sleeve 63 are screwed off completely, the tobacco liquid is injected into the liquid reservoir 502 via the liquid injection hole 97. After the injection of the tobacco liquid is finished, the external screw sleeve 63 is screwed on, and the pushing element 92 is pushed by the air pipe 80 upon the force exerted by the external screw sleeve 63. In this position, the liquid guiding hole 98 is opened, and the liquid reservoir 502 communicates with the liquid guiding chamber 902. Therefore, the tobacco liquid in the liquid reservoir 502 flows from the liquid reservoir 502 to the liquid guiding chamber 902 via the liquid guiding hole 98. Accordingly, serious liquid leakage, which occurs due to a difference in pressure of the atmosphere between inside and outside of the atomizing tube 50, is prevented.

It is to be understood that in other embodiments, the internal screw sleeve 61 and the external screw sleeve 63 may be coupled by other ways, e.g., plug type.

It is to be understood that in other embodiments, the atomizing tube 50 may be made of transparent material, so that quantity of the tobacco liquid left in the atomizing tube 50 may be seen through the atomizing tube 50.

Figure 3:
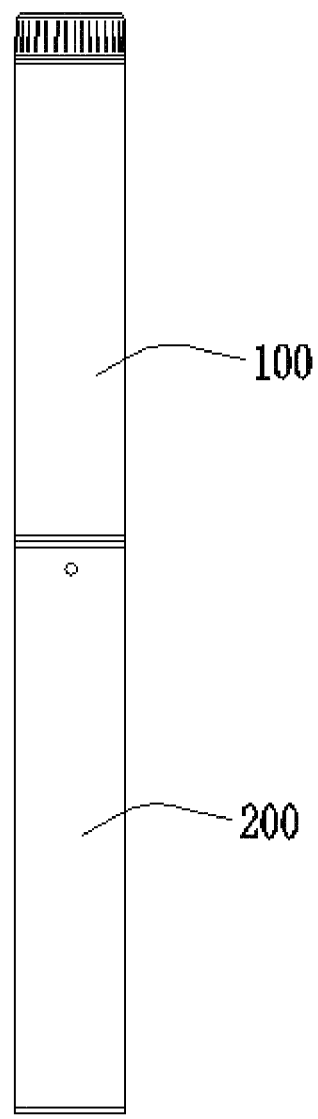
FIG. 3 is a side view of an electronic cigarette according to a second embodiment.

Referring to FIG. 3, an electronic cigarette includes an atomizer 100 and a battery assembly 200. The battery assembly 200 is connected to the atomizer 100, and configured for powering the atomizer 100.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for an electronic cigarette, comprising:
an atomizing tube;
an atomizing assembly;
a first fixing sleeve arranged at a first end of the atomizing tube;
a fixing tube received in the first end of the atomizing tube adjacent to the first fixing sleeve, the fixing tube receiving the atomizing assembly and being connected to the first fixing sleeve, the atomizing tube defining a liquid reservoir, the fixing tube defining a liquid guiding chamber;
an air pipe and a second fixing sleeve, wherein the second fixing sleeve is arranged at a second end of the atomizing tube opposite to the first end, the fixing tube comprises a top wall defining an opening, a first end of the air pipe passes through the opening, and is connected with the atomizing assembly, a second end of the air pipe is held against the second fixing sleeve, and an outer wall of the air pipe and an inner wall of the opening cooperatively define a liquid guiding hole;
wherein the second fixing sleeve comprises an internal screw sleeve, and an external screw sleeve engaged with the internal screw sleeve, the internal screw sleeve is fixedly connected with the atomizing tube, the internal screw sleeve and the air pipe cooperatively define a liquid injection hole, and the atomizer further comprises a seal sleeve configured for sealing the liquid injection hole; and
a spring and a pushing element in the fixing tube, wherein the pushing element sequentially comprises a first tube body, a flange, and a second tube body, the first tube body is connected with the atomizing assembly, the second tube body is fixedly connected with the air pipe, a first end of the spring abuts against the first fixing sleeve, an opposite second end of the spring abuts against the flange, and the pushing element is configured for moving upwards or downwards to open or close the liquid guiding hole upon an external force.

2. The atomizer of claim 1, further comprising a silicone ring wrapped around the first tube body.

3. The atomizer of claim 1, further comprising a seal ring wrapped around the second tube body, the seal ring is configured for sealing the liquid guiding hole.

4. The atomizer of claim 1, wherein a stroke of the pushing element is less than that of the external screw sleeve.

5. The atomizer of claim 1, wherein the atomizing assembly comprises a tube, a fixing sleeve for fixing a heating wire, a heating wire component, and a cover, the tube is fixedly connected with the first fixing sleeve, the heating wire component is fixed in the fixing sleeve, the fixing sleeve is engaged in the tube, the cover covers the heating wire component and the fixing sleeve, and fixes the heating wire component and the fixing sleeve in the tube.

6. The atomizer of claim 1, wherein the atomizing tube is made of transparent material.

7. An electronic cigarette comprising:
an atomizer according to claim 1; and
a battery assembly, the atomizer being connected to the battery assembly.

8. An atomizer for an electronic cigarette, comprising:
an atomizing tube;
an atomizing assembly;
a first fixing sleeve arranged at a first end of the atomizing tube;
a fixing tube received in the first end of the atomizing tube adjacent to the first fixing sleeve, the fixing tube receiving the atomizing assembly and being connected to the first fixing sleeve, the atomizing tube defining a liquid reservoir, the fixing tube defining a liquid guiding chamber; and
an air pipe, wherein the fixing tube comprises a top wall defining an opening, and an outer wall of the air pipe and an inner wall of the opening cooperatively define a liquid guiding hole; wherein the atomizer further comprises a spring and a pushing element in the fixing tube, the pushing element sequentially comprises a first tube body, a flange, and a second tube body, the first tube body is connected with the atomizing assembly, the second tube body is fixedly connected with the air pipe, a first end of the spring abuts against the first fixing sleeve, an opposite second end of the spring abuts against the flange, and the pushing element is configured for moving upwards or downwards to open or close the liquid guiding hole upon an external force.

9. The atomizer of claim 8, further comprising a silicone ring wrapped around the first tube body.

10. The atomizer of claim 8, further comprising a seal ring wrapped around the second tube body, the seal ring is configured for sealing the liquid guiding hole.

11. An electronic cigarette comprising:
an atomizer comprising:
an atomizing tube;
an atomizing assembly;
a first fixing sleeve arranged at a first end of the atomizing tube; and
a fixing tube received in the first end of the atomizing tube adjacent to the first fixing sleeve, the fixing tube receiving the atomizing assembly and being connected to the first fixing sleeve, the atomizing tube defining a liquid reservoir, the fixing tube defining a liquid guiding chamber; and
an air pipe, wherein the fixing tube comprises a top wall defining an opening, and an outer wall of the air pipe and an inner wall of the opening cooperatively define a liquid guiding hole; wherein the atomizer further comprises a spring and a pushing element in the fixing tube, the pushing element sequentially comprises a first tube body, a flange, and a second tube body, the first tube body is connected with the atomizing assembly, the second tube body is fixedly connected with the air pipe, a first end of the spring abuts against the first fixing sleeve, an opposite second end of the spring abuts against the flange, and the pushing element is configured for moving upwards or downwards to open or close the liquid guiding hole upon an external force; and a battery assembly, the atomizer being connected to the battery assembly.

12. The electronic cigarette of claim 11, further comprising a silicone ring wrapped around the first tube body.

13. The electronic cigarette of claim 11, further comprising a seal ring wrapped around the second tube body, the seal ring is configured for sealing the liquid guiding hole.

* * * * *